United States Patent
Birk et al.

(10) Patent No.: US 9,316,605 B2
(45) Date of Patent: Apr. 19, 2016

(54) DETERMINATION OF ATTRIBUTES OF LIQUID SUBSTANCES

(75) Inventors: Uzi Birk, Huddinge (SE); David Livshits, San Francisco, CA (US); Rotem Rabinovich, Uttran (SE)

(73) Assignee: DELAVAL HOLDING AB, Tumba (SE)

(*) Notice: Subject to any disclaimer, the term of this patent is extended or adjusted under 35 U.S.C. 154(b) by 485 days.

(21) Appl. No.: 13/820,615

(22) PCT Filed: Sep. 22, 2010

(86) PCT No.: PCT/EP2010/063966
§ 371 (c)(1),
(2), (4) Date: Mar. 4, 2013

(87) PCT Pub. No.: WO2012/037974
PCT Pub. Date: Mar. 29, 2012

(65) Prior Publication Data
US 2013/0173180 A1    Jul. 4, 2013

(51) Int. Cl.
*G01N 33/04* (2006.01)
*G01N 27/02* (2006.01)

(52) U.S. Cl.
CPC .............. *G01N 27/023* (2013.01); *G01N 33/04* (2013.01)

(58) Field of Classification Search
CPC ... G01N 27/02; G01N 27/023; G01N 27/026; G01N 27/00; G01N 33/04; G01R 27/00; G01R 27/02
See application file for complete search history.

(56) References Cited

U.S. PATENT DOCUMENTS

| 3,566,841 | A | 3/1971 | Gerrish et al. |
| 4,010,715 | A | 3/1977 | Robar et al. |
| 4,678,995 | A | 7/1987 | Avison et al. |
| 6,315,955 | B1 | 11/2001 | Klein |
| 6,511,851 | B1 | 1/2003 | Payne et al. |
| 6,782,736 | B1 * | 8/2004 | Hammer ............... 73/61.44 |

(Continued)

FOREIGN PATENT DOCUMENTS

| AU | 428 035 B2 | 9/1972 |
| DE | 41 34 549 A1 | 4/1993 |

(Continued)

OTHER PUBLICATIONS

Mukhopadhyay S C et al.: "Low Cost Sensing System for Dairy Products Quality Monitoring" Instrumentation and Measurement Technology Conference, 2005, IMTC 2005, Proceedings of the IEEE Ottawa, ON, Canada May 16-19, 2005, Piscataway, NJ, USA, IEEE, vol. 1, May 16, 2005, pp. 244-249, XP010900391, DOI: DOI:10, 1109/IMTC.2005,1604109 ISBN: 978-0-7803-8879-6 the whole document, cited in ISR.

(Continued)

*Primary Examiner* — Toan Le
(74) *Attorney, Agent, or Firm* — Young & Thompson

(57) ABSTRACT

A monitoring unit (100) that determines parameters (p1, p2) of an attribute (P) of a liquid substance flowing (F) through a dielectric conduit (110) includes plural coil members (121, 122) encircling the dielectric conduit (110) that subjects a flow of the liquid substance to plural different electromagnetic fields (B(f)), and under influence thereof measuring circuitry registers corresponding impedance measures (z(f)) of the liquid substance. A processor (130) derives the parameters (p1, p2) of the attribute (P) based on the registered impedance measures (z(f)).

19 Claims, 3 Drawing Sheets

(56) References Cited

U.S. PATENT DOCUMENTS

| | | |
|---|---|---|
| 7,141,978 B2 | 11/2006 | Peck et al. |
| 7,219,024 B2 | 5/2007 | Gamache et al. |
| 2008/0104306 A1 | 5/2008 | Lee et al. |
| 2009/0129982 A1 | 5/2009 | Rapoport |
| 2009/0278685 A1 | 11/2009 | Potyrailo et al. |
| 2011/0068807 A1* | 3/2011 | Kesil et al. .................. 324/633 |

FOREIGN PATENT DOCUMENTS

| | | |
|---|---|---|
| EP | 2480878 A1 | 8/2012 |
| NL | 9 400 997 A | 2/1996 |
| RU | 2196985 C2 | 1/2003 |
| RU | 2205382 C2 | 5/2003 |
| RU | 2284592 C2 | 9/2006 |
| SU | 1 603 277 A1 | 10/1990 |
| SU | 1741055 A1 | 6/1992 |
| WO | 00/39578 A2 | 7/2000 |
| WO | 2004/096974 A2 | 11/2004 |
| WO | 2008/076453 A1 | 6/2008 |
| WO | 2011038003 A1 | 3/2011 |

OTHER PUBLICATIONS

Supplemental International Search Report, dated Jan. 17, 2013, from corresponding PCT application.

International Search Report, dated Jun. 17, 2011, from corresponding PCT application.

European Office Action, dated Jul. 10, 2014, from corresponding EP application.

* cited by examiner

DETERMINATION OF ATTRIBUTES OF LIQUID SUBSTANCES

THE BACKGROUND OF THE INVENTION AND PRIOR ART

The present invention relates generally to automatic determination of at least one attribute of a liquid substance. More particularly, the invention relates to a monitoring unit, a method, and a computer readable medium.

There are many areas where efficient and reliable handling of liquid substances is important, for instance in connection with production and processing of foodstuffs. Moreover, automatic milking solutions are becoming increasingly efficient and sophisticated. Today, there is also a strong demand for flexible and animal-friendly milk production. For example, so-called milking robots have been introduced, which enable animals to autonomously decide when they are to be milked. Milking robots are advantageous because they reduce the amount of manual labor involved in milking. Milking robots are also desirable from an animal health point-of-view, since thereby it is uncomplicated to extract milk more frequently than by applying the existing alternative solutions, and in general, high-frequency milking vouches for a good udder health. However, milking robots may be somewhat problematic because these machines are often operated without any human operator being present. This, in turn, renders a safe and reliable operation highly important. One aspect of such an operation is that problems related to unsatisfying milk quality must be resolved automatically. For example it is necessary to automatically detect unacceptably high concentrations certain constituents in the milk, such that adequate measures can be taken promptly.

U.S. Pat. No. 4,678,995 describes an apparatus and method for determining the presence of specific substances in a sample, e.g. of tissue, by nuclear magnetic resonance (NMR) and then obtaining a high-resolution NMR image of these substances.

U.S. Pat. No. 7,141,978 discloses a solution for analyzing fluid samples by means of an NMR probe comprising multiple NMR detection sites.

WO 00/39578 reveals a method and apparatus for estimation of a cell count in a body fluid. Here, a mid-IR spectrum is recorded and the spectral information therein serves as a basis for deriving a number of cells in the body fluid. This document also briefly mentions the possibility to employ NMR spectroscopy.

US 2009/0278685 describes methods and systems for calibration of radio-frequency identification (RFID) sensors involving impedance measuring by determining a complex impedance spectrum, a phase angle and/or a magnitude of the impedance. Inter alia, the document mentions that the RFID sensors may be adapted to measure physical, chemical and biological parameters; each sensor can have a digital ID and be calibrated to accurately react to a parameter of interest through changes in measurements of the sensor's complex impedance.

U.S. Pat. No. 7,219,024 discloses a system, method and program product for determining in-place engineering properties, such as density and moisture content of certain engineering materials. A database, material model and sensor model are also shown. The document generally relates to material analysis, and to the field of impedance spectroscopy, and the determination of engineering properties of a material from the response to electromagnetic probing in a defined frequency spectrum.

U.S. Pat. No. 6,511,851 reveals a method for identifying a change in the composition of a liquid. Here, a time varying electrical or electromagnetical input signal is applied to the liquid in a range of frequencies encompassing a resonant frequency of an electrical circuit comprising the liquid. An impedance quantity is measured of said electrical circuit by means of the output signal as a function of the frequency of the time varying input signal in said range of frequencies. A resonant frequency of said electrical circuit is determined. After a change in the composition of the liquid, variation in the impedance quantity is measured at or near the previously determined resonant frequency of said electrical circuit. The variation in the impedance quantity is then related to the change in the composition.

WO 2008/076453 describes a flex fuel sensor, which is deployed in conjunction with a fuel transfer line, or at the bottom/side of a fuel tank. A radio-frequency signal at a constant frequency may be generated across a resonant circuit, which comprises an inductor and a printed circuit board trace capacitor, capacitor plates, semi cylindrical capacitor plates, or the like. Electromagnetic radiation is propagated into the passing fuel in the transfer pipe. The conductivity and dielectric properties of the fuel change the capacitance of the trace capacitor plates. These changes are proportional to the ethanol/alcohol content of the fuel, and are preferably detected by a microcontroller, or the like, and then transmitted to a flex fuel vehicle engine management system.

Problems Associated with the Prior Art

Hence, diverse solutions are known for determining various properties of different kinds of entities (e.g. represented by tissue pieces, fluid samples or RFID sensors). However, there is yet no straightforward solution for unobtrusive online monitoring of the characteristics a flowing liquid.

SUMMARY OF THE INVENTION

The object of the present invention is to alleviate the above problem, and thus offer an efficient solution for determining a measure representing an attribute of a flowing liquid substance, for instance in the form of a liquid food product.

According to one aspect of the invention, the object is achieved by the initially described monitoring unit, wherein the unit includes a dielectric conduit, a measuring circuitry and a processor. The dielectric conduit is configured to transport a flow of the liquid substance through the monitoring unit. The measuring circuitry includes a coil member encircling the dielectric conduit. The measuring circuitry is further configured to register an impedance measure of the liquid substance when flowing through the dielectric conduit. The processor is configured to derive the attribute of the liquid substance based on the registered impedance measure.

This monitoring unit is advantageous because in addition to allowing continuous monitoring in real time, the unit is straightforward to install, uncomplicated to operate, and since no consumables are required, essentially maintenance free.

According to one preferred embodiment of this aspect of the invention, the determined attribute contains a first number of different parameters and the first number is larger than or equal to two. The monitoring unit further includes at least one dielectric conduit and a second number of measuring circuitries. The at least one dielectric conduit is configured to transport the flow of the liquid substance through the monitoring unit. The second number, in turn, is larger than or equal to the first number. Further, each measuring circuitry includes a coil member encircling one of the at least one dielectric conduit, and each measuring circuitry is configured to register a respective impedance measure of the liquid substance when flowing through said one of the at least one dielectric conduit in response an electromagnetic field applied to the liquid substance via the at least one coil member. Here, the processor is configured to derive each of the first number of parameters based on the registered impedance measures. Such a design is advantageous because it provides convenient monitoring of multiple constituents and/or characteristics of the liquid substance.

According to another preferred embodiment of this aspect of the invention, the coil member in each measuring circuitry is configured to apply an electromagnetic field having a particular spectral range. The total number of different spectral ranges of electromagnetic energy applied to the liquid substance via the coil members is here larger than or equal to the first number. Preferably, each electromagnetic field has a relatively narrow spectral range with a distinct center frequency located in an interval from 1 MHz to 1500 MHz. Thus, for example one constituent/characteristic per center frequency of the liquid substance can be determined.

According to yet another preferred embodiment of this aspect of the invention, the processor is associated with a data bank of coefficients describing relationships between impedance measures of the liquid substance and the different parameters. The processor is here configured to derive said parameters by applying analytic calculations and/or numerical methods to equations describing relationships between the impedance measures and the different parameters. Thereby, a comparatively large number of constituents and/or characteristics of the liquid substance can be determined in a relatively uncomplicated manner.

According to still another preferred embodiment of this aspect of the invention, the processor is associated with a lookup table describing relationships between impedance measures of the liquid substance and the different parameters of said attribute, and the processor is configured to derive said parameters from said lookup table, either directly or by interpolating between values therein. Hence, a comparatively large number of constituents and/or characteristics of the liquid substance can be determined in a very processing efficient manner.

According to a further preferred embodiment of this aspect of the invention, the determined attribute of the liquid substance includes one or more of the parameters: water content, a concentration of sodium, the total concentration of solids, pH level and electrical conductivity. Consequently, the proposed monitoring unit is generally well suited for online checking of liquid food products.

According to another preferred embodiment of this aspect of the invention, the liquid substance is presumed to be milk, and the determined attribute includes one or more of the parameters: a concentration of lactose, a concentration of fat, a concentration of protein, a concentration of urea and a concentration of somatic cells. Further preferably, parameters reflecting a concentration of macrophages, leucocytes and/or polymorphonuclear leukocytes may also be determined. Hence, the monitoring unit is especially adapted for employment in conjunction with a milking installation, for example to prevent mixing of poor-quality milk with good milk.

According to still a further preferred embodiment of this aspect of the invention, each measuring circuitry includes a power source and an interface. The power source is configured to generate electric energy to the coil member, such that in response thereto the coil member produces an electromagnetic field having a particular spectral range. The interface is configured to enable the processor to register the impedance measure of the measuring circuitry. This renders the overall design exceptionally uncomplicated.

According to yet another preferred embodiment of this aspect of the invention, the monitoring unit includes at least two parallel dielectric conduits, each of which is configured to transport a fraction of the flow of liquid substance. Each dielectric conduit is also encircled by at least one coil member of a respective one of said measuring circuitries. Thus, the monitoring unit can be made physically compact.

According to another aspect of the invention, the object is achieved by the method described initially, wherein a flow of the liquid substance is transported through a dielectric conduit. When the liquid substance is flowing there through, the liquid substance is subjected to the electromagnetic field, an impedance measure is registered, and based thereon said attribute is derived. The advantages of this method, as well as the preferred embodiments thereof, are apparent from the discussion above with reference to the proposed monitoring unit.

According to a further aspect of the invention the object is achieved by a computer program, which is directly loadable into the memory of a computer, and includes software adapted to implement the method proposed above when said program is run on a computer.

According to another aspect of the invention the object is achieved by a computer readable medium, having a program recorded thereon, where the program is to control a computer to perform the method proposed above when the program is loaded into the computer.

Further advantages, beneficial features and applications of the present invention will be apparent from the following description and the dependent claims.

BRIEF DESCRIPTION OF THE DRAWINGS

The invention is now to be explained more closely by means of preferred embodiments, which are disclosed as examples, and with reference to the attached drawings.

DESCRIPTION OF PREFERRED EMBODIMENTS OF THE INVENTION

Figure 1:
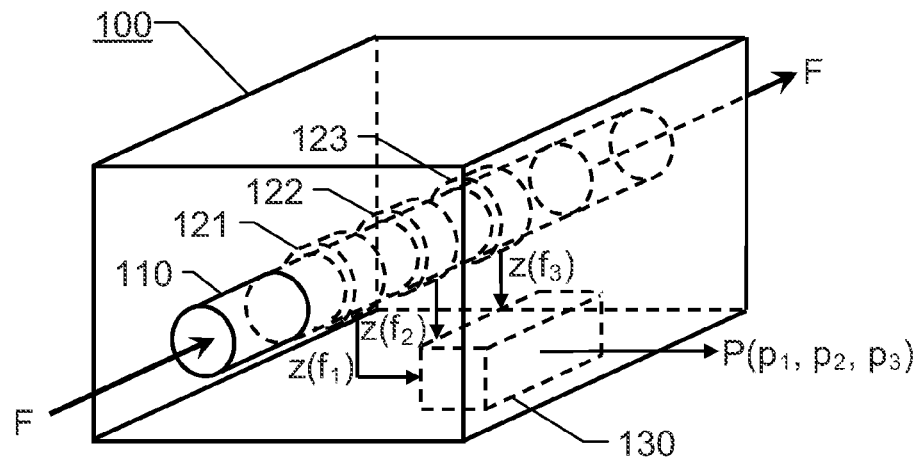
FIG. 1 shows a perspective view of a monitoring unit according to a first embodiment of the invention.

Methods for detecting constituents in liquids, primary water based solutions, may use the change in water's permittivity ($\in$>80) at electromagnetic wave frequencies in the range 1 MHz to 200 MHz. These methods are strongly dependent on the concentrations of impurities in the water. Since knowing only the dielectric property is insufficient to draw a conclusion regarding the concentration levels of individual elements, the present invention proposes that dielectric spectroscopy (DS) be applied.

In general, DS (which may also be referred to as impedance spectroscopy) measures the dielectric properties of a medium as a function of frequency. DS is based on the interaction of an external field with the electric dipole moment of a liquid sample. This interaction is often expressed by permittivity.

There are a number of different dielectric mechanisms connected to the way a studied medium reacts to an applied electromagnetic field. Each dielectric mechanism is centered on its characteristic frequency, which is the reciprocal of the characteristic time of the process. Normally, the dielectric mechanisms are divided into relaxation processes and resonance processes, and the most common dielectric mechanisms are: dipole relaxation (in the MHz-to-GHz range), ionic relaxation (in the kHz range) and dielectric relaxation (in the kHz-to-GHz range). The working frequencies for the present invention are in the MHz range, and therefore dipole relaxation and dielectric relaxation are primarily involved.

Dipole relaxation originates from permanent and induced dipoles aligning to an electric field. The orientation of the dipoles' polarization is disturbed by thermal noise (which misaligns the dipole vectors from the overall direction of the field), and the time needed for the dipoles to relax is determined by the local viscosity of the liquid medium. This renders dipole relaxation heavily dependent on temperature and chemical environment. The polarization of a dielectric material is a competition between torques due to the imposed electric field, which tends to align the molecules; and collisions, which tend to destroy the alignment.

Dielectric relaxation as a whole is the result of the movement of dipoles, i.e. dipole relaxation. Dielectric relaxation is the momentary delay, or lag, in the dielectric constant of a material. This is usually caused by the delay in the molecular polarization with respect to a changing electric field in a dielectric medium.

Ionic relaxation as a whole is the result of electric charges moving due to an applied alternating field. The time lag between electrical field and polarization implies an irreversible degradation of free energy. In physics, dielectric relaxation typically refers to the relaxation response of a dielectric medium to an external electric field of microwave frequencies. Such a relaxation is often described in terms of permittivity as a function of frequency.

The theory of DS gives us an understanding that an electromagnetical field can influence different molecules, and even cells, at a variety of frequencies being unique to each type of molecule or cell. This phenomenon allows quantifying a majority of the components and contaminants in a liquid substance.

We now refer to FIG. 1, which shows a perspective view of a monitoring unit 100 for determining an attribute P of a liquid substance according to a first embodiment of the invention.

The monitoring unit 100 includes measurement means, a dielectric conduit 110 and a processor 130. The measurement means, which here include coil members 121, 122 and 123, are configured to subject a liquid substance flowing F through the dielectric conduit 110 to an electromagnetic field. Under influence of the electromagnetic field, the measurement means are further configured to measure at least one electromagnetic property of the liquid substance, namely register impedance measures $z(f_1)$, $z(f_2)$ and $z(f_3)$ respectively. To achieve the electromagnetic influence and enable said measurements, each of the coil members 121, 122 and 123 includes at least one electric conductor loop encircling the dielectric conduit 110. Preferably, to avoid interference the coil members 121, 122 and 123 are also electromagnetically screened from one another.

Figure 2:
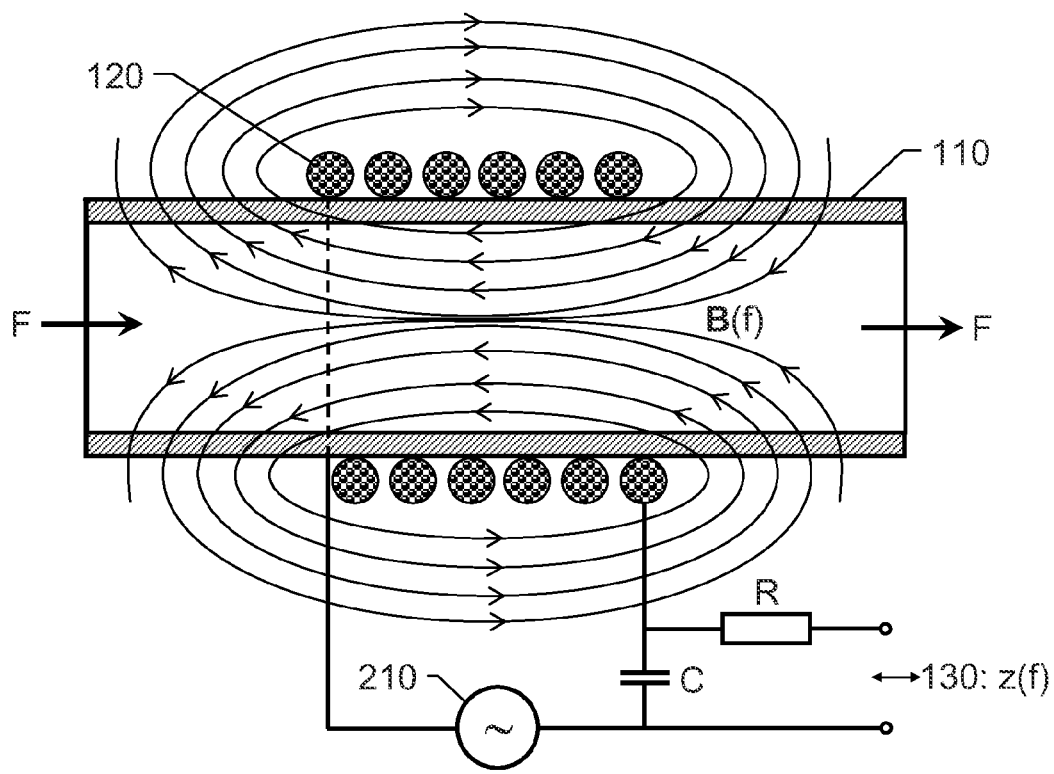
FIG. 2 shows a schematic side view of a measuring circuitry according to one embodiment of the invention.
Figure 3:
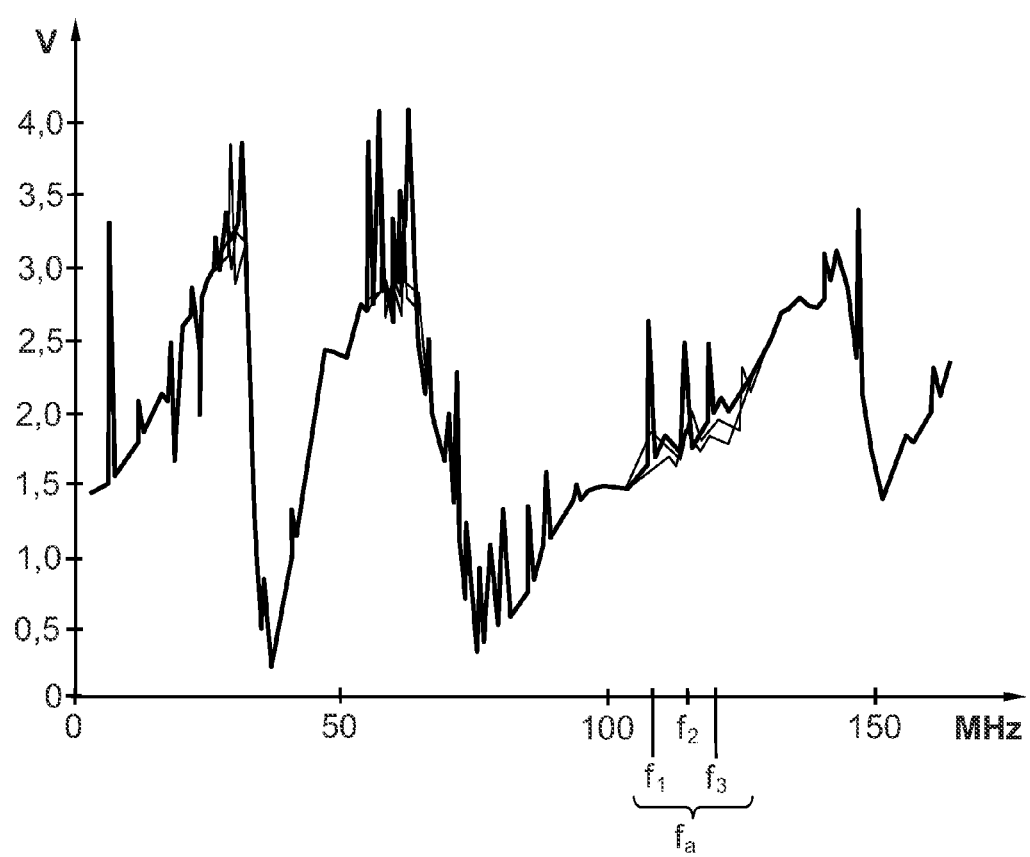
FIG. 3 shows graphs representing a respective measured voltage as a function of frequency for each of five different milk samples.

The processor 130 is configured to derive the above-mentioned attribute P based on the registered impedance measures $z(f_1)$, $z(f_2)$ and $z(f_3)$. If the attribute P only includes one parameter it is sufficient that the measurement means contains a single measuring circuitry. FIG. 2 shows an example of such a design, which will be used to explain operating principle of the monitoring unit according to the invention.

In FIG. 2, a schematic measuring circuitry and dielectric conduit 110 are shown in a side view. As can be seen the coil member 120 here contains six loops of an electric conductor around the dielectric conduit 110.

A power source 210 is connected to the coil member 120 and configured to deliver electric energy to the coil member 120. Consequently, in response to the electric energy, the coil member 120 produces an electromagnetic field B(f), which has a particular spectral range f and extends into the dielectric conduit 110. Depending on the characteristics of the liquid substance flowing F through dielectric conduit 110, the electromagnetic field B(f) will experience particular impedance. The measuring circuitry further includes an interface, here represented by symbolic resistive and capacitive components R and C respectively, towards the processor 130 through which interface the processor 130 is enabled to register an impedance measure z(f) reflecting the impedance experienced by the electromagnetic field B(f). Thereby, the processor 130 may determine the attribute P of the liquid substance, as well as detect any variations in the characteristics relating to this attribute P.

Returning now to FIG. 1, we see that the attribute P contains a first number of different parameters denoted $p_1$, $p_2$ and $p_3$ respectively. The first number is larger than or equal to two. In this example, the first number is three.

The parameters $p_1$, $p_2$ and $p_3$ of the attribute P may represent various characteristics and/or constituents of the liquid substance, such as water content, a concentration of sodium, the total concentration of solids, pH level and electrical conductivity. Provided that the liquid substance is milk, the parameters $p_1$, $p_2$ and $p_3$ may further reflect a concentration of lactose, a concentration of fat, a concentration of protein, a concentration of urea and/or a concentration of somatic cells.

In any case, a second number of measuring circuitries are included in the monitoring unit 100, where the second number is larger than or equal to the first number. In other words, at least as many measuring circuitries are included as the number of parameters $p_1$, $p_2$ and $p_3$ that shall be determined. This relationship will be explained in further detail below. In the embodiment of FIG. 2, the attribute P contains three parameters $p_1$, $p_2$ and $p_3$, and therefore three coil members 121, 122 and 123 respectively encircle the dielectric conduit 110. In response the electromagnetic fields applied to the liquid substance via the coil members 121, 122 and 123, each measuring circuitry is configured to register a respective impedance measure $z(f_1)$, $z(f_2)$ and $z(f_3)$ of the liquid substance when flowing F through the dielectric conduit 110. It is should be noted that there is typically not a direct relationship between a particular impedance measure $z(f_1)$, $z(f_2)$ or $z(f_3)$ and a given parameter $p_1$, $p_2$ or $p_3$. Instead, inter alia due to various interference and combinatory effects, the relations between the impedance measure $z(f_1)$, $z(f_2)$ and $z(f_3)$ and the parameters $p_1$, $p_2$ and $p_3$ are best described by an equation system. To avoid underdetermination, the number of impedance measures is larger than or equal to the number of parameters. The equation system, in turn, may be fairly complex and can for instance include non-linear components. Nevertheless, based on the registered impedance measures $z(f_1)$, $z(f_2)$ and $z(f_3)$ and said relations, the processor 130 is configured to derive each of the parameters $p_1$, $p_2$ and $p_3$.

To illustrate how the relations between the impedance measures $z(f_1)$, $z(f_2)$ and $z(f_3)$ and the parameters $p_1$, $p_2$ and $p_3$ may be determined we will now refer to a simple linear example. For different concentrations of constituents in the liquid substance corresponding to each parameter $p_1$, $p_2$ and $p_3$, a respective impedance measure is registered, for instance via impedance spectroscopy (IS). Here, the energy storage and energy dissipation of the liquid substance is probed over a range of frequencies, say from 1 MHz to 1500 MHz, by means of impedance measurements. These measurements may be carried out using a so-called potentiostat instrument. Since essentially all physio-chemical systems (e.g. solutions, organic molecules and biological tissue) possess such energy storage and dissipation properties it is possible to characterize a given physio-chemical system through its impedance response to a particular electromagnetic frequency. Consequently, before the monitoring unit 100 is used for measurement purposes, liquid substance is transported through the unit with various known concentrations $p_1$, $p_2$ and $p_3$ of constituents therein, and for each concentration an impedance measure $z(f_1)$, $z(f_2)$ and $z(f_3)$ is registered while the liquid substance is subjected to an electromagnetic field having a selected frequency (or spectral range) $f_1$, $f_2$ and $f_3$ respectively, which has been found to be particularly impedance sensitive with respect to the constituent in question.

This can be described as:

$$\begin{pmatrix} z(f_1) \\ z(f_2) \\ z(f_3) \end{pmatrix} = \begin{pmatrix} k_{11} & k_{12} & k_{13} \\ k_{21} & k_{22} & k_{23} \\ k_{31} & k_{32} & k_{33} \end{pmatrix} \begin{pmatrix} p_1 \\ p_2 \\ p_3 \end{pmatrix},$$

or more compact:

$$Z = K \cdot P.$$

Thus, the attribute P, representing the parameters $p_1$, $p_2$ and $p_3$, can be derived as:

$$P = K^{-1} \cdot Z$$

which may also be expressed:

$$\begin{pmatrix} p_1 \\ p_2 \\ p_3 \end{pmatrix} = \begin{pmatrix} k_{22}k_{33} - k_{23}k_{32} & k_{13}k_{32} - k_{12}k_{33} & k_{12}k_{23} - k_{13}k_{22} \\ k_{23}k_{31} - k_{21}k_{33} & k_{11}k_{33} - k_{13}k_{31} & k_{13}k_{21} - k_{11}k_{23} \\ k_{21}k_{32} - k_{22}k_{31} & k_{12}k_{31} - k_{11}k_{33} & k_{11}k_{22} - k_{12}k_{21} \end{pmatrix} \begin{pmatrix} z(f_1) \\ z(f_2) \\ z(f_3) \end{pmatrix},$$

or in general terms:

$$P = \frac{1}{\det(K)} (adj(K)) \cdot Z.$$

According to the invention, the total number of different spectral ranges of electromagnetic energy applied to the liquid substance via the coil members 121, 122 and 123 is larger than or equal to the first number. Of course, for large numbers of parameters $p_i$ of the attribute P, fairly extensive calculations may be required. This is especially true if (in contrast to the above example) the relationships between parameters $p_i$ and the impedance measures $z_i$ are non-linear. For relatively few parameters $p_i$ and uncomplicated relationships, however, a lookup table can be a useful tool. For somewhat more complex equation systems, analytic calculations may prove to be more efficient, whereas determining the parameters $p_i$ in especially intricate cases may require various numerical methods.

According to one embodiment of the invention, the processor 130 is associated with a data bank of coefficients describing the relationships between impedance measures $z(f_1)$, $z(f_2)$ and $z(f_3)$ of the liquid substance and the different parameters $p_1$, $p_2$ and $p_3$ of the attribute P. Here, the processor 130 is configured to derive the parameters $p_1$, $p_2$ and $p_3$ by applying analytic calculations and/or numerical methods to equations describing relationships between the impedance measures $z(f_1)$, $z(f_2)$ and $z(f_3)$ of the liquid substance and the different parameters $p_1$, $p_2$ and $p_3$.

According to another embodiment of the invention, the processor 130 is associated with a lookup table describing relationships between impedance measures $z(f_1)$, $z(f_2)$ and $z(f_3)$ of the liquid substance and the different parameters $p_1$, $p_2$ and $p_3$ of the attribute P. The processor 130 is here configured to derive the parameters $p_1$, $p_2$ and $p_3$ from said lookup table, either directly or by interpolating between values therein.

In any case, to further illustrate how to obtain the above-mentioned matrix $K^{-1}$ needed to derive the attribute P and any parameters $p_i$ thereof, we will now discuss a general example.

Let us assume that n designated coil members, or sensors, are to be used, and that the below linear system of equations describe the relationships between n different parameters $p_1$, $p_2$, ..., $p_n$ of a liquid substance to be determined, coefficients $b_1, b_2, \ldots, b_n$ represent respective weight coefficients of the n sensors, $c_1, c_2, \ldots, c_n$ designate respective constants for the n sensors, and $z(f_1), z(f_2), \ldots, z(f_n)$ are the respective readings of the n sensors.

$$\begin{aligned} z(f_1) &= a_1 b_{11} + a_2 b_{12} + a_3 b_{13} + \ldots + a_n b_{1n} + c_1 \\ z(f_2) &= a_1 b_{21} + a_2 b_{22} + a_3 b_{23} + \ldots + a_n b_{2n} + c_2 \\ &\ldots \qquad \ldots \\ z(f_n) &= a_1 b_{n1} + a_2 b_{n2} + a_3 b_{n3} + \ldots + a_n b_{nn} + c_n \end{aligned}$$

To determine the n weight coefficients $b_1, b_2, \ldots, b_n$ and the respective constant for each sensor, i.e. $c_1, c_2, \ldots, c_n$ it is necessary to study n+1 different samples with known composition of the liquid substance.

Thus, for the first sensor, the following system of linear equations shall be solved:

$$\begin{aligned} z(f_1) &= a_{11} b_{11} + a_{12} b_{12} + a_{13} b_{13} + \ldots + a_{1n} b_{1n} + c_1 \\ z(f_2) &= a_{21} b_{11} + a_{22} b_{12} + a_{23} b_{13} + \ldots + a_{2n} b_{1n} + c_1 \\ &\ldots \qquad \ldots \\ z(f_{n+1}) &= a_{(n+1)1} b_{11} + a_{(n+1)2} b_{12} + a_{(n+1)3} b_{13} + \ldots + a_{(n+1)n} b_{1n} + c_1 \end{aligned}$$

where:

$a_{11}, a_{12}, \ldots, a_{1n}, a_{2n}, \ldots, a_{(n+1)n}$ are n known portions of components, or parameters, in n+1 respective samples of the liquid substance;

$b_{11}, b_{12}, \ldots, b_{1n}$ are n weight coefficients of the n known portions of components, or parameters, for the first sensor to be determined;

$c_1$ is the constant of the first sensor to be determined; and $z(f_1), z(f_2), \ldots, z(f_{n+1})$ are the respective readings of the first sensor for the n+1 known samples.

Analogously, for the second sensor, the following system of linear equations should be solved:

$$z(f_1) = a_{11}b_{21} + a_{12}b_{22} + a_{13}b_{23} + \ldots + a_{1n}b_{2n} + c_2$$
$$z(f_2) = a_{21}b_{21} + a_{22}b_{22} + a_{23}b_{23} + \ldots + a_{2n}b_{2n} + c_2$$
$$\ldots \qquad \ldots$$
$$z(f_{n+1}) = a_{(n+1)1}b_{21} + a_{(n+1)2}b_{22} + a_{(n+1)3}b_{23} + \ldots + a_{(n+1)n}b_{2n} + c_2$$

where:

$a_{11}, a_{12}, \ldots, a_{1n}, a_{2n}, \ldots, a_{(n+1)n}$ are n known portions of components, or parameters, in n+1 respective samples of the liquid substance;

$b_{21}, b_{22}, \ldots, b_{2n}$ are n weight coefficients of the n known portions of components, or parameters, for the second sensor to be determined;

$c_2$ is the constant of the second sensor to be determined; and $z(f_1)$, $z(f_2)$, $z(f_{n+1})$ are the respective readings of the second sensor for the n+1 known samples.

Similarly, for the n:th sensor, the following system of linear equations is to be solved:

$$z(f_1) = a_{11}b_{n1} + a_{12}b_{n2} + a_{13}b_{n3} + \ldots + a_{1n}b_{nn} + c_n$$
$$z(f_2) = a_{21}b_{n1} + a_{22}b_{n2} + a_{23}b_{n3} + \ldots + a_{2n}b_{nn} + c_n$$
$$\ldots \qquad \ldots$$
$$z(f_{n+1}) = a_{(n+1)1}b_{n1} + a_{(n+1)2}b_{n2} + a_{(n+1)3}b_{n3} + \ldots + a_{(n+1)n}b_{nn} + c_n$$

where:

$a_{11}, a_{12}, \ldots, a_{1n}, a_{2n}, \ldots, a_{(n+1)n}$ are n known portions of components, or parameters, in n+1 respective samples of the liquid substance;

$b_{n1}, b_{n2}, \ldots, b_{nn}$ are n weight coefficients of the n known portions of components, or parameters, for the n:th sensor to be determined;

$c_n$ is the constant of the n:th sensor to be determined; and $z(f_1)$, $z(f_2)$, $z(f_{n+1})$ are the respective readings of the n:th sensor for the n+1 known samples.

Preferably, according to embodiments of the present invention, a computer program is used for calculating the attribute P, i.e. the parameters $p_i$, such as various component concentrations in the liquid substance. The computer program may be based on the so-called Gaussian elimination method. Thereby, first the method is used for solving systems of linear equations in which unknown factors are the weight coefficients and the known factors are the samples data $a_{nm}$ and the sensor readings $z(f_k)$. Second, the method is used to verify the calculated weight coefficients $b_{ij}$. In this case, unknown factors are the parameters $p_i$, and known factors are the weight coefficients $b_{ij}$ and the sensor readings $z(f_k)$.

Figure 4:
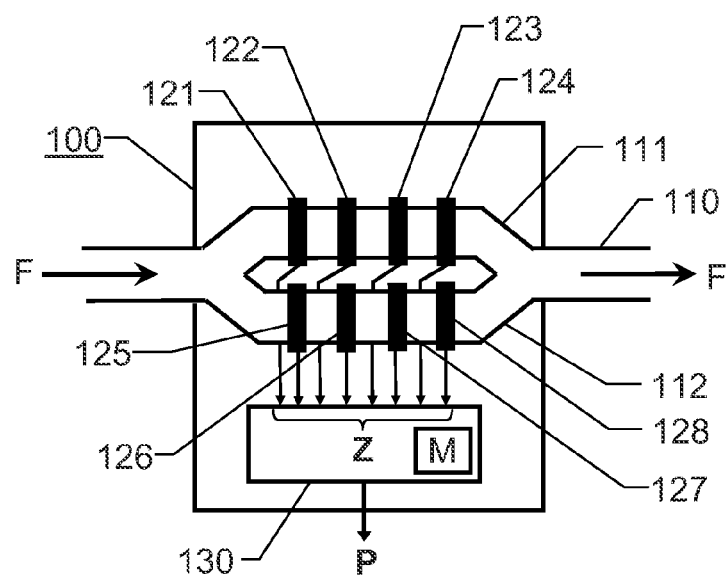
FIG. 4 schematically illustrates a monitoring unit according to a second embodiment of the invention.

According to one embodiment of the present invention, the liquid substance is represented by milk, e.g. from cows. By using a standard potentiostat, areas may be identified where an electrical field influences specific milk components. FIG. 4 shows a respective graph over five different milk samples scanned in a frequency range from 10 MHz to 170 MHz. Each graph represents a measured voltage over a sensor coil as a function of frequency for a given milk sample. Hence, the voltage reflects any impedance variations in the milk in response to the variation in frequency. As can be seen, there is a substantial overlap among the graphs. However, there are also frequency areas where the graphs split in amplitude. These are areas where phenomena of impedance spectroscopy take place, and consequently the influence of each individual constituent in the milk can be defined. In this case, a frequency area $f_a$ was found especially interesting. To identify the most suitable frequencies, two milk samples were used with the minimum and maximum concentrations of a target constituent. Hence, to identify the best frequency for monitoring fat content, milk samples were used which had 0% fat (skim milk) and 3.2% fat (pasteurized milk) respectively. Analogously, two milk samples were used which both had 3.2% fat (pasteurized milk and farm milk respectively), but which had great difference in somatic cell count (SCC) to define an appropriate frequency where SCC has the strongest response; and finally, two milk samples were used that contained 3.2% pasteurized lactose free milk and 3.2% pasteurized regular milk to find a frequency where lactose has the strongest response.

Using the potentiostat, in this case it was determined that at a first frequency $f_1$, around 117 MHz, sufficient sensitivity was obtained for measuring lactose; at a second frequency $f_2$, around 126 MHz, sufficient sensitivity was obtained for measuring SCC; and at a third frequency $f_3$, around 131 MHz, sufficient sensitivity was obtained for measuring milk fat. Based on this information, in turn, measuring circuitries were designed, which are optimized for registering parameters around the identified frequencies $f_1$, $f_2$ and $f_3$ respectively.

Table 1 below shows an example of impedance measurements on milk samples in respect of fat content, lactose content, content of solids non-fat (SNF), direct microscopic somatic cell count (DMSCC×1000), milk urea nitrogen (MUN) content, true protein content (i.e. compensated for non-nitrogen protein), content of other solids and the total content of solids. Here, the deviations are relatively small for all parameters, except for the direct microscopic somatic cell count. Therefore, for all parameters other than the direct microscopic somatic cell count, the dependence of milk impedance on them can be assumed to be linear. On the other hand, among the samples the difference in the direct microscopic somatic cell count runs up to tenfold numbers. Consequently, the dependence of milk impedance on this parameter cannot be assumed linear. Instead, to take proper account of the milk impedance behavior on the direct microscopic somatic cell count a $(DMSCC \times 1000)^2$ column has been added to Table 1.

TABLE 1

| Fat (%) | Total Protein (%) | Lactose (%) | SNF (%) | DMSCC × 1000 | MUN (mg/dl) | True protein (%) | Other solids (%) | Total solids (%) | (DMSCC × $1000)^2$ |
|---|---|---|---|---|---|---|---|---|---|
| 3.38 | 3.07 | 4.82 | 8.61 | 180 | 16.4 | 2.88 | 5.73 | 11.99 | 32400 |
| 3.85 | 3.13 | 4.79 | 8.64 | 389 | 13.7 | 2.94 | 5.7 | 12.49 | 151321 |
| 3.47 | 3.1 | 4.76 | 8.58 | 190 | 14.9 | 2.91 | 5.67 | 12.05 | 36100 |
| 3.18 | 3.07 | 4.77 | 8.56 | 222 | 9.3 | 2.88 | 5.68 | 11.74 | 49284 |
| 4.16 | 3.33 | 4.89 | 8.94 | 180 | 12 | 3.14 | 5.8 | 13.1 | 32400 |
| 4.53 | 3.72 | 4.75 | 9.19 | 188 | 7.6 | 3.53 | 5.66 | 13.72 | 35344 |
| 3.73 | 3.42 | 4.9 | 9.04 | 160 | 11.4 | 3.23 | 5.81 | 12.77 | 25600 |
| 3.56 | 3.23 | 4.7 | 8.65 | 1025 | 12.8 | 3.04 | 5.61 | 12.21 | 1050625 |
| 5.08 | 3.38 | 4.53 | 8.63 | 730 | 11.8 | 3.19 | 5.44 | 13.71 | 532900 |
| 2.96 | 3.4 | 4.85 | 8.97 | 130 | 11.2 | 3.21 | 5.76 | 11.93 | 16900 |
| 3.48 | 3.05 | 4.81 | 8.58 | 118 | 12.6 | 2.86 | 5.72 | 12.06 | 13924 |
| 3.67 | 3.3 | 4.75 | 8.77 | 705 | 12.6 | 3.11 | 5.66 | 12.44 | 497025 |

Table 2 below represents the result of measurements on milk samples made by a set of measuring circuitries, which each includes at least one coil member of the proposed type. Each measuring circuit here measured a resonance amplitude and resonance frequency respectively. According to the invention, both these values can be used for weight coefficient determination.

TABLE 2

| Resonance amplitudes | | | | Resonance frequencies | | | |
|---|---|---|---|---|---|---|---|
| Coil #4 (mV) | Coil #8 (mV) | Coil #20 (mV) | Coil #73 (mV) | Coil #4 (MHz) | Coil #8 (MHz) | Coil #20 (MHz) | Coil #73 (MHz) |
| 5331.21 | 7050 | 7783.48 | 10002.5 | 145.23 | 91.033 | 36.873 | 9.479 |
| 5336.14 | 7046.87 | 7770.98 | 9930.14 | 145.223 | 91.058 | 36.887 | 9.489 |
| 5322.98 | 7052.79 | 7800.26 | 9981.79 | 145.206 | 91.067 | 36.876 | 9.487 |
| 5372.33 | 7107.08 | 7608.13 | 9448.5 | 145.262 | 91.079 | 36.928 | 9.485 |
| 5327.59 | 7056.74 | 7633.79 | 9566.61 | 145.212 | 91.112 | 36.909 | 9.484 |
| 5351.93 | 7077.47 | 7697.94 | 9673.2 | 145.213 | 91.079 | 36.949 | 9.492 |
| 5302.91 | 7007.06 | 7827.23 | 9964.69 | 145.179 | 90.937 | 36.859 | 9.48 |
| 5221.98 | 6933.7 | 7848.62 | 10021.6 | 145.168 | 91.016 | 36.82 | 9.478 |
| 5324.95 | 7055.1 | 7776.9 | 9890.99 | 145.224 | 90.99 | 36.921 | 9.488 |
| 5326.27 | 7029.44 | 7766.04 | 9909.09 | 145.222 | 91.031 | 36.899 | 9.491 |
| 5299.29 | 7042.27 | 7697.94 | 9765.65 | 145.222 | 91.063 | 36.891 | 9.476 |

As mentioned earlier, weight coefficients are preferably calculated and verified for each coil member used. In this example, using all 12 samples, the following data were obtained.

| Coil #2 | | Coil #3 | |
|---|---|---|---|
| Coef #0 | −269.972 | Coef #0 | 82.7843 |
| Coef #1 | 1494.87 | Coef #1 | −783.27 |
| Coef #2 | −870.284 | Coef #2 | 365.625 |
| Coef #3 | 0.127788 | Coef #3 | 0.611944 |
| Coef #4 | 32.4042 | Coef #4 | −9.53335 |
| Coef #5 | −0.00032 | Coef #5 | −0.00037 |
| Coef #6 | 10457.7 | Coef #6 | 6782.92 |

| Coil #1 (frequency) | | Coil #3 (frequency) | |
|---|---|---|---|
| Coef #0 | −0.18802 | Coef #0 | −0.02558 |
| Coef #1 | 1.35308 | Coef #1 | −0.06935 |
| Coef #2 | −0.91157 | Coef #2 | 0.1982 |
| Coef #3 | −0.00014 | Coef #3 | 8.12E−06 |
| Coef #4 | 0.030247 | Coef #4 | 0.007431 |
| Coef #5 | −7.93E−08 | Coef #5 | −4.65E−08 |
| Coef #6 | 149.208 | Coef #6 | 35.405 |

| Coil #2 (frequency) | | Coil #4 (frequency) | |
|---|---|---|---|
| Coef #0 | −0.0711 | Coef #0 | 0.01687 |
| Coef #1 | 0.44809 | Coef #1 | −0.15115 |
| Coef #2 | −0.22186 | Coef #2 | 0.109708 |
| Coef #3 | 0.000268 | Coef #3 | −6.03E−06 |
| Coef #4 | 0.003958 | Coef #4 | −0.00196 |
| Coef #5 | −3.83E−07 | Coef #5 | 1.26E−08 |
| Coef #6 | 91.7391 | Coef #6 | 8.97722 |

Table 3 below shows the values of Table 1 after correction according to the above weight coefficients #0, #1, #2, #3, #4, #5 and #6 for the coil members #1, #2, #3 and #4.

TABLE 3

| Fat (%) | Total Protein (%) | SNF (%) | DMSCC × 1000 | MUN (mg/dl) | (DMSCC × 1000)² |
|---|---|---|---|---|---|
| 3.38 | 3.07 | 8.61 | 180 | 16.4 | 32400 |
| 4.2 | 3.34633 | 8.74 | 603.083 | 12.41 | 466175 |

TABLE 3-continued

| Fat (%) | Total Protein (%) | SNF (%) | DMSCC × 1000 | MUN (mg/dl) | (DMSCC × 1000)² |
|---|---|---|---|---|---|
| 3.32 | 3.04862 | 8.56 | 88.2551 | 10.65 | −55225.6 |
| 3.18 | 3.07 | 8.56 | 222 | 9.3 | 49284 |
| 3.83 | 3.52021 | 9.06 | 105.543 | 9.589 | 55371.5 |
| 4.53 | 3.72 | 9.19 | 188 | 7.6 | 35344 |
| 3.73 | 3.42 | 9.04 | 160 | 11.4 | 25600 |
| 3.56 | 3.23 | 8.65 | 1025 | 12.8 | 1.05E+06 |
| 5.08 | 3.38 | 8.63 | 730 | 11.8 | 532900 |
| 3.58 | 3.19371 | 8.75 | 531.161 | 15.22 | 487567 |
| 3.48 | 3.05 | 8.58 | 118 | 12.6 | 13924 |
| 5.31 | 3.82474 | 9.18 | 691.621 | 11.64 | 538136 |

Two different strategies are proposed to check the consistency of the weight coefficients. The consistency can be proved by calculating weight coefficients of selected parameters of the liquid substance (e.g. the above milk components) using different sets of samples. Then, if the coefficients are sufficiently close, it is safe to assume that these coefficients are "correct", and may therefore be used for real/live measurements on a liquid substance.

An alternative way to prove the consistency of the components' weight coefficients is to use the coefficients for calculating a number of parameters of the liquid substance for samples which were not used in order to determine the coefficients, and then compare the calculated parameters with the measured data.

If the liquid substance is milk, SCC is one of the most important parameters to characterize the quality of this liquid food product. Today, various methods based on photoluminescence are employed for counting the number of somatic cells in milk samples. However, said methods cannot easily distinguish between different types of leukocytes. Namely, in milk there are 4 to 6 major groups of somatic cells, which differ in terms function, size and electrical polarization. Typically, in uninfected milk with a SCC less than 300,000 we find the following concentrations of somatic cells: macrophages 60%, leucocytes 28% and polymorphonuclear leukocytes (PMN) 5-25%. Nevertheless, if the milk originates from an animal having mastitis, the SCC is normally above 400,000, and here the concentration of PMN may be as high as 90% (usually in a range from 33% to 49%). Hence, by studying parameters related to leukocytes a more accurate measure of the animal health can be obtained than by monitoring SCC alone. Different leukocytes have different polarization frequencies, and may thus be individually identified via the present invention.

FIG. 4 schematically illustrates a monitoring unit 100 according to an embodiment of the invention, wherein the dielectric conduit 110 has been spilt into two separate branches 111 and 112 respectively. This enables a relatively compact design of the monitoring unit 100. Naturally, any number of parallel branches is here conceivable if further compactness is desired. In any case, each branch 111 and 112 is configured to transport a fraction of the flow F, and each branch is encircled by at least one coil member 121, 122, 123 and 124 respective 125, 126, 127 and 128, which coil member is included in a measuring circuitry. Preferably, for sensitivity reasons the electromagnetic field produced by each coil member has a relatively narrow spectral range with a distinct center frequency that is located in an interval from 1 MHz to 1500 MHz. Thus, based on the coil members 121, 122, 123, 124, 125, 126, 127 and 128 up to eight parameters of the attribute P can be determined by the processor 130.

It is also preferable if the processor 130 includes, or is associated with, a computer readable medium M, e.g. in the form of a memory module, such that the processor 130 has access to the contents of this medium M. Furthermore, a program is recorded in the computer readable medium M, and the program is adapted to make the processor 130 control the process described above, as well as the embodiments thereof further elaborated on below, when the program is run on the processor.

Figure 5:
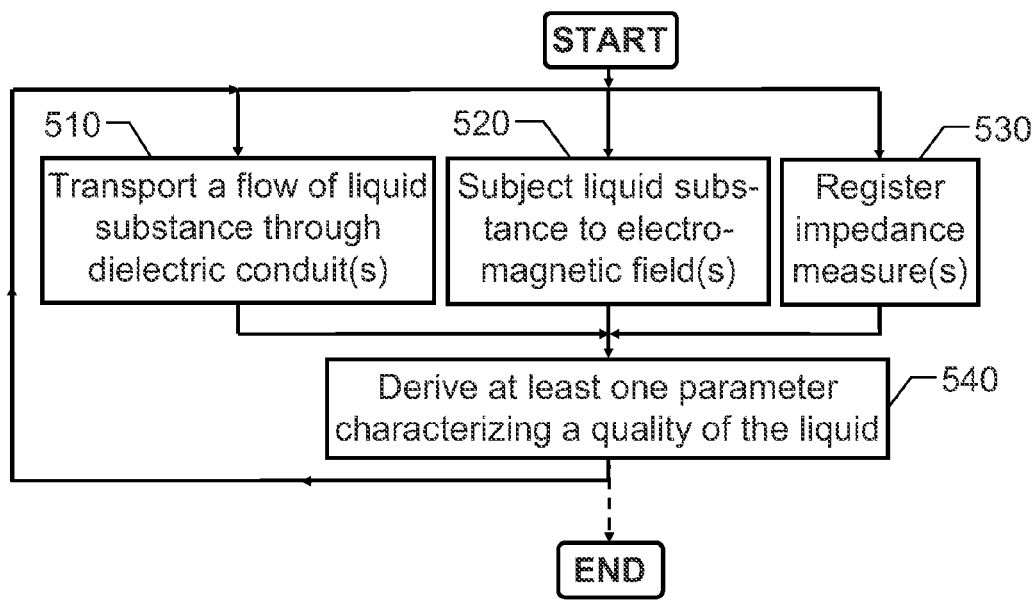
FIG. 5 illustrates, by means of a flow diagram, the general method according to the invention.

In order to sum up, we will now describe the general method according to the invention with reference to the flow diagram in FIG. 5.

In a first step 510, a flow of liquid substance is transported through at least one dielectric circuit. In parallel there with, a step 520 subjects the liquid substance to at least one electromagnetic field having a respective spectral range. A step 530 parallel with steps 510 and 520, registers at least one impedance measure, or more precisely registers a number of impedance measures equal to the number of electromagnetic fields applied in step 520.

Then, based on the registered impedance measures, a step 540 determines at least one parameter characterizing an attribute of the liquid substance. More precisely, step 540 determines up to as many parameters as the number of impedance measures registered in step 530.

Thereafter, the procedure either ends, or loops back to steps 510 to 530 for continued measuring and updating of the at least one parameter.

All of the process steps, as well as any sub-sequence of steps, described with reference to FIG. 5 above may be controlled by means of a programmed computer apparatus. Moreover, although the embodiments of the invention described above with reference to the drawings comprise computer apparatus and processes performed in computer apparatus, the invention thus also extends to computer programs, particularly computer programs on or in a carrier, adapted for putting the invention into practice. The program may be in the form of source code, object code, a code intermediate source and object code such as in partially compiled form, or in any other form suitable for use in the implementation of the process according to the invention. The program may either be a part of an operating system, or be a separate application. The carrier may be any entity or device capable of carrying the program. For example, the carrier may comprise a storage medium, such as a Flash memory, a ROM (Read Only Memory), for example a DVD (Digital Video/Versatile Disk), a CD (Compact Disc) or a semiconductor ROM, an EPROM (Erasable Programmable Read-Only Memory), an EEPROM (Electrically Erasable Programmable Read-Only Memory), or a magnetic recording medium, for example a floppy disc or hard disc. Further, the carrier may be a transmissible carrier such as an electrical or optical signal which may be conveyed via electrical or optical cable or by radio or by other means. When the program is embodied in a signal which may be conveyed directly by a cable or other device or means, the carrier may be constituted by such cable or device or means. Alternatively, the carrier may be an integrated circuit in which the program is embedded, the integrated circuit being adapted for performing, or for use in the performance of, the relevant processes.

Although the invention has been described in relation to the analysis of milk, it is equally well adapted for analyzing other liquids, especially other liquid food products. The parameters to be analyzed will in those cases of course be different than the ones described in this specification.

Although the invention is advantageous in connection with cow milking, the invention is equally well adapted for implementation in milking machines for any other kind of mammals, such as goats, sheep or buffaloes.

The term "comprises/comprising" when used in this specification is taken to specify the presence of stated features, integers, steps or components. However, the term does not preclude the presence or addition of one or more additional features, integers, steps or components or groups thereof.

The invention is not restricted to the described embodiments in the figures, but may be varied freely within the scope of the claims.

The invention claimed is:

1. A monitoring unit (100) for determining an attribute (P) of a liquid substance, comprising:
    a dielectric conduit (110);
    a processor (130) configured to determine said attribute (P), said attribute (P) containing a first number of different parameters (p1, p2, p3), the first number being larger than or equal to two;
    a measurement element (120) comprising a second number of measuring circuits, the second number being larger than or equal to the first number,
    each measuring circuit comprising a coil member (121, 122, 123) encircling the dielectric conduit (110) and connected to the processor (130),
    each coil member (121, 122, 123) being configured to produce a respective electromagnetic field (B(f1), B(f2), B(f3)) at a spectral range (f1, f2, f3) different from the other coil members (121, 122, 123),
    each of the coil members (121, 122, 123) subjecting the liquid substance, flowing through the dielectric conduit (110), to a respective one of the electromagnetic fields (B(f1), B(f2), B(f3)) of the respective different spectral range (f1, f2, f3),
    when under influence of the electromagnetic fields (B(f1), B(f2), B(f3)), each of the coil members (121, 122, 123) producing a respective impedance measure (z(f1), z(f2), z(f3)) of the liquid substance, flowing through said dielectric conduit, (110) in response the electromagnetic field (B(f)) applied to the liquid substance via each said coil member (121, 122, 123),
    wherein the processor registers each impedance measure (z(f1), z(f2), z(f3)) and derives each of the first number of parameters (p1, p2, p3) based on the registered impedance measures (z(f1), z(f2), z(f3)), each of the parameters (p1, p2, p3) being derived from a plurality of the registered impedance measures (z(f1), z(f2), z(f3)).

2. The monitoring unit (100) according to claim 1, wherein a total number of different spectral ranges of electromagnetic energy applied to the liquid substance is larger than or equal to the first number.

3. The monitoring unit (100) according to claim 2, wherein each electromagnetic field (B(f)) has a spectral range (f1, f2, f3) with a different center frequency located in an interval from 1 MHz to 1500 MHz.

4. The monitoring unit (100) according to claim 1, wherein,
the processor (130) is associated with a data bank of coefficients describing relationships between the impedance measures (z(f1), z(f2), z(f3)) of the liquid substance and the different parameters (p1, p2, p3) of said attribute (P), and
the processor (130) is configured to derive said parameters (p1, p2, p3) by applying at least one of analytic calculations and numerical methods to equations describing relationships between the impedance measures (z(f1), z(f2), z(f3)) of the liquid substance and the different parameters (p1, p2, p3).

5. The monitoring unit (100) according to claim 1, wherein, the processor (130) is associated with a lookup table describing relationships between the impedance measures (z(f1), z(f2), z(f3)) of the liquid substance and the different parameters (p1, p2, p3) of said attribute (P), and the processor (130) is configured to derive said parameters (p1, p2, p3) from said lookup table, either directly or by interpolating between values therein.

6. The monitoring unit (100) according to claim 1, wherein said parameters (p1, p2, p3) comprise at least one of a water content, a concentration of sodium, a pH level, and an electrical conductivity.

7. The monitoring unit (100) according to claim 1, wherein, the liquid substance is milk, and
said parameters (p1, p2, p3) comprise at least one of a concentration of lactose, a concentration of fat, a concentration of protein, a concentration of urea, and a concentration of somatic cells.

8. The monitoring unit (100) according to claim 7, wherein said parameters (p1, p2, p3) further comprise at least one of a concentration of macrophages, a concentration of leucocytes and a concentration of polymorphonuclear leukocytes.

9. The monitoring unit (100) according to claim 1, wherein each measuring circuitry comprises:
a power source (210) configured to generate electric energy to the coil member (120), such that in response thereto the coil member (120) produces the electromagnetic field (B(f)) having the particular spectral range (f), and
an interface (R, C) connecting to the processor (130) through which interface (R, C) the processor (130) is enabled to register said impedance measure (z(f)).

10. The monitoring unit (100) according to claim 1,
comprising at least two of said dielectric conduit (110),
the dielectric conduits (111, 112) being arranged in parallel with each other,
each of the dielectric conduits (111, 112) configured to transport a fraction of a flow (F) of the liquid substance, and
each of the dielectric conduits (111, 112) being encircled by at least of the one coil members (121, 122, 123, 124; 125, 126, 127, 128) of a respective one of said measuring circuitries.

11. A method for determining an attribute (P) of a liquid substance, said attribute (P) containing a first number of different parameters (p1, p2, p3), the first number being larger than or equal to two, the method comprising:
subjecting a flow (F) of the liquid substance, being transported through a dielectric conduit (110), to a second number of electromagnetic fields (B(f1), B(f2), B(f3)), the second number being larger than or equal to the first number, each of the electromagnetic fields (B(f1), B(f2), B(f3)) having a different spectral range (f1, f2, f3);
registering, in response the applied electromagnetic fields (B(f1), B(f2), B(f3)), corresponding impedance measures (z(f1), z(f2), z(f3)) of the liquid substance flowing through the dielectric conduit (110); and
deriving said attribute (P) based on the registered impedance measures (z(f1), z(f2), z(f3)),
wherein said subjecting step uses a measurement element (120) comprising the second number of measuring circuits,
each measuring circuit comprising a coil member (121, 122, 123) encircling the dielectric conduit (110) and connected to output to a processor (130),
each coil member (121, 122, 123) being configured to produce a respective one of the electromagnetic fields (B(f1), B(f2), B(f3)) at the respective spectral range (f1, f2, f3) different from the other coil members (121, 122, 123),
each of the coil members (121, 122, 123) subjecting the liquid substance, flowing through the dielectric conduit (110), to a respective one of the electromagnetic fields (B(f1), B(f2), B(f3)) of the respective different spectral range (f1, f2, f3),
when under influence of the electromagnetic fields (B(f1), B(f2), B(f3)), each of the coil members (121, 122, 123) producing a respective one of the impedance measures (z(f1), z(f2), z(f3)) of the liquid substance flowing through said dielectric conduit (110) in response the electromagnetic field (B(f)) applied to the liquid substance via each said coil member (121, 122, 123), and
wherein in said registering step the processor registers each impedance measure (z(f1), z(f2), z(f3)) and derives each of the first number of parameters (p1, p2, p3) based on the registered impedance measures (z(f1), z(f2), z(f3)), each of the parameters (p1, p2, p3) being derived from a plurality of the registered impedance measures (z(f1), z(f2), z(f3)).

12. The method according to claim 11, wherein, a total number of different spectral ranges of electromagnetic energy applied to the liquid substance via the coil members (121, 122, 123) is larger than or equal to the first number.

13. The method according to claim 12, wherein each electromagnetic field (B(f)) has a spectral range (f1, f2, f3) with a different distinct center frequency located in an interval from 1 MHz to 1500 MHz.

14. The method according to claim 11, comprising the further step of:
deriving said parameters (p1, p2, p3) by applying at least one of analytic calculations and numerical methods to a system of equations describing relationships between the impedance measures (z(f1), z(f2), z(f3)) of the liquid substance and the different parameters (p1, p2, p3) of said attribute (P).

15. The method according to claim 11, comprising the step of:
deriving said parameters (p1, p2, p3) from a lookup table describing relationships between the impedance measures (z(f1), z(f2), z(f3)) of the liquid substance and the different parameters (p1, p2, p3) of said attribute (P), either directly or by interpolating between values therein.

16. The method according to claim 11, wherein said parameters (p1, p2, p3) comprise at least one of a water content, a concentration of sodium, a pH level, and an electrical conductivity.

17. The method according to claim 11, wherein,
the liquid substance is milk, and
said parameters (p1, p2, p3) comprise at least one of a concentration of lactose, a concentration of fat, a concentration of protein, a concentration of urea, and a concentration of somatic cells.

18. The method according to claim 17, wherein said parameters (p1, p2, p3) further comprise at least one of a concentration of macrophages, a concentration of leucocytes and a concentration of polymorphonuclear leukocytes.

19. A non-transitory computer readable medium storing thereon a computer program loadable into memory (M) of a computer, the computer program comprising software for controlling the computer to perform a method for determining an attribute (P) of a liquid substance, said attribute (P) containing a first number of different parameters (p1, p2, p3), the first number being larger than or equal to two, the method comprising:
subjecting a flow (F) of the liquid substance, being transported through a dielectric conduit (110), to a second number of electromagnetic fields (B(f1), B(f2), B(f3)), the second number being larger than or equal to the first number, each of the electromagnetic fields (B(f1), B(f2), B(f3)) having a different spectral range (f1, f2, f3);
registering, in response the applied electromagnetic fields (B(f1), B(f2), B(f3)), corresponding impedance measures (z(f1), z(f2), z(f3)) of the liquid substance when flowing through the dielectric conduit (110); and
deriving said attribute (P) based on the registered impedance measures (z(f)),
wherein said subjecting step uses a measurement element (120) comprising the second number of measuring circuits,
each measuring circuit comprising a coil member (121, 122, 123) encircling the dielectric conduit (110) and connected to output to a processor (130),
each coil member (121, 122, 123) being configured to produce a respective one of the electromagnetic fields (B(f1), B(f2), B(f3)) at the respective spectral range (f1, f2, f3) different from the other coil members (121, 122, 123),
each of the coil members (121, 122, 123) subjecting the liquid substance, flowing through the dielectric conduit (110), to a respective one of the electromagnetic fields (B(f1), B(f2), B(f3)) of the respective different spectral range (f1, f2, f3),
when under influence of the electromagnetic fields (B(f1), B(f2), B(f3)), each of the coil members (121, 122, 123) producing a respective one of the impedance measures (z(f1), z(f2), z(f3)) of the liquid substance flowing through said dielectric conduit (110) in response the electromagnetic field (B(f)) applied to the liquid substance via each said coil member (121, 122, 123), and
wherein in said registering step the processor registers each impedance measure (z(f1), z(f2), z(f3)) and derives each of the first number of parameters (p1, p2, p3) based on the registered impedance measures (z(f1), z(f2), z(f3)), each of the parameters (p1, p2, p3) being derived from a plurality of the registered impedance measures (z(f1), z(f2), z(f3)).

* * * * *